US00PP15929P2

(12) United States Plant Patent
Gossett

(10) Patent No.: US PP15,929 P2
(45) Date of Patent: Aug. 23, 2005

(54) *HEUCHERA* PLANT NAMED 'CITY LIGHTS'

(50) Latin Name: ***Heuchera* hybrid**
Varietal Denomination: City Lights

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 91 days.

(21) Appl. No.: 10/871,806

(22) Filed: Jun. 18, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP8,965 P * 11/1994 Heims ..... Plt./263
PP15,085 P2 * 8/2004 Oliver ..... Plt./263

OTHER PUBLICATIONS http://www.terranovanurseries.com/pages/plantsH3.html.*

* cited by examiner

*Primary Examiner*—Kent Bell
*Assistant Examiner*—W. C. Haas
(74) *Attorney, Agent, or Firm*—Klarquist Sparkman, LLP

(57) ABSTRACT

A new and distinct hybrid of *Heuchera* plant characterized by a compact habit, dark leaves, and cream-colored flowers.

1 Drawing Sheet

Botanical classification: *Heuchera* hybrid.
Variety denomination: 'City Lights'.

The present invention relates to a new and distinct cultivar of *Heuchera* hybrid and given the cultivar name of 'City Lights'. *Heuchera* is in the family Saxifragaceae. *Heuchera* 'City Lights' originated from a cross between unknown parents. This new *Heuchera* was selected from seedlings grown from select interspecfic hybrids that were unnamed, experimental varieties that were open pollinated in the field in Canby, Oreg.

This new *Heuchera* is distinguished by:

1. Medium size, dark leaves which are shiny in the spring.
2. Cream colored flowers.
3. Compact habit.
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with changes in environment without a change in the genotype of the plant.

BRIEF DESCRIPTION OF THE DRAWING

The drawing shows *Heuchera* 'City Lights' growing in the trial beds in spring in Canby, Oreg.

DETAILED PLANT DESCRIPTION

The following is a detailed description of the new *Heuchera* cultivar based on observations of a one year old specimen grown in the ground in full sun under typical outdoor conditions in the trial fields in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: *Heuchera* hybrid.
Variety denomination: 'City Lights'.

Plant:

*Form.*—Basal rosette, herbaceous perennial.
*Hardiness.*—USDA Zone 4 to 9.
*Size.*—23 cm tall from the ground to the top of the foliage and 35 cm wide.
*Vigor.*—Excellent.
*Roots.*—Fibrous, freely branching, fine, and white in color. Roots develop easily from cuttings.
*Habit.*—Mound.

Leaf:

*Type.*—Simple.
*Arrangement.*—Rosette.
*Shape.*—Broadly ovate.
*Lobing/division.*—5 shallow rounded lobes, with 1 to 2 shallow secondary lobes.
*Venation.*—Palmate.
*Margins.*—Crenate.
*Apex.*—Obtuse.
*Base.*—Cordate, lobes overlapping at the base.
*Blade size.*—8.5 cm long and 7.5 cm wide.
*Surface texture.*—Thin and leathery with sparse, glandular hairs on both the upper and lower surfaces and with the vein velutinous.
*Petiole size.*—19 to 22 cm and 2 to 3 mm wide.
*Petiole surface texture.*—Covered with velutinous hairs.
*Petiole color.*—Red Purple 185A.
*Leaf color.*—Summer abaxial — Purpled silver with green veins. Grey 201 with areas of Greyed Purple 185C and with Yellow Green.147A veins in a reticulate pattern. Spring abaxial — Between Greyed Purple 187A and Brown 200A. Adaxial — Greyed Purple 187B.

Inflorescence:

*Type.*—Thyrse.

*Number of flowers.*—200 per thyrse.

*Number of thyrse in first flush in spring.*—10.

*Peduncle.*—With 0 to 2 petiolate cauline leaves, ovate, 4 to 6.5 cm long and 3.5 to 6 cm wide. Height — 44 to 74 cm. Diameter — 0.3 to 0.4 cm near base. Color — Greyed Orange 177A. Surface texture — Velutinous.

*Pedicel.*—Length — 0.2 to 0.4 cm. Surface texture — Glandular puberulent. Color — Red Purple 59A.

*Bloom period.*—May through June in Canby, Oreg.

Flower bud:

*Size.*—0.3 cm wide and 0.4 cm long.

*Description.*—Glandular puberulent, ovoid.

*Color.*—Yellow Green 145A to C.

Flower:

*Type.*—Perfect, zygomorphic.

*Shape.*—Campanulate.

*Size.*—0.6 cm long and 0.4 cm wide.

*Petal count.*—5, inconspicuous.

*Petal color.*—White 155D on both surfaces.

*Petal shape.*—Spatulate, entire, with a clawed base and acute tip.

*Petal size.*—0.3 cm long.

*Calyx.*—5 lobes, ovate, entire, with an acute tip, divided ½ way to the base, with glandular hairs.

*Calyx size.*—0.6 cm long and 0.4 cm wide.

*Calyx and flower color.*—Greyed Yellow 160B at base and very tip and Yellow White 158A in middle. The color is the same on both surfaces, except slightly darker on the outside surface.

*Stamen.*—5 in number, with filaments 2.5 mm long, White 155A, anthers oval, no pollen, male sterile.

*Pistil.*—One, typical of the genus, with the style 2.5 mm long, Yellow Green 145C, 2-branched stigma Yellow Green 145C, ovary greenish white, closest to Yellow Green 145D.

*Fragrance.*—None.

*Lastingness.*—Each thryse blooms for about 2 weeks on the plant.

Fruit:

*Type.*—Two-beaked ovoid capsule.

*Fertility.*—Low.

*Color.*—Brown 200D.

Seed:

*Shape.*—Linear.

*Size.*—2 mm. long.

*Color.*—Black. RHS 202A.

Disease and pest tolerance: Excellent disease resistance to powdery mildew, the common problem of *Heuchera*. Susceptible to root weevils.

COMPARISON TO SIMILAR *HEUCHERA*

Compared to *Heuchera* 'Chocolate Ruffles' (U.S. Plant Pat. No. 8,965), *Heuchera* 'City Lights' has showy cream-colored flower rather than insignificant wind pollinated flowers and unruffled leaves rather than ruffled leaves.

I claim:

1. A new and distinct *Heuchera* plant as herein illustrated and described.

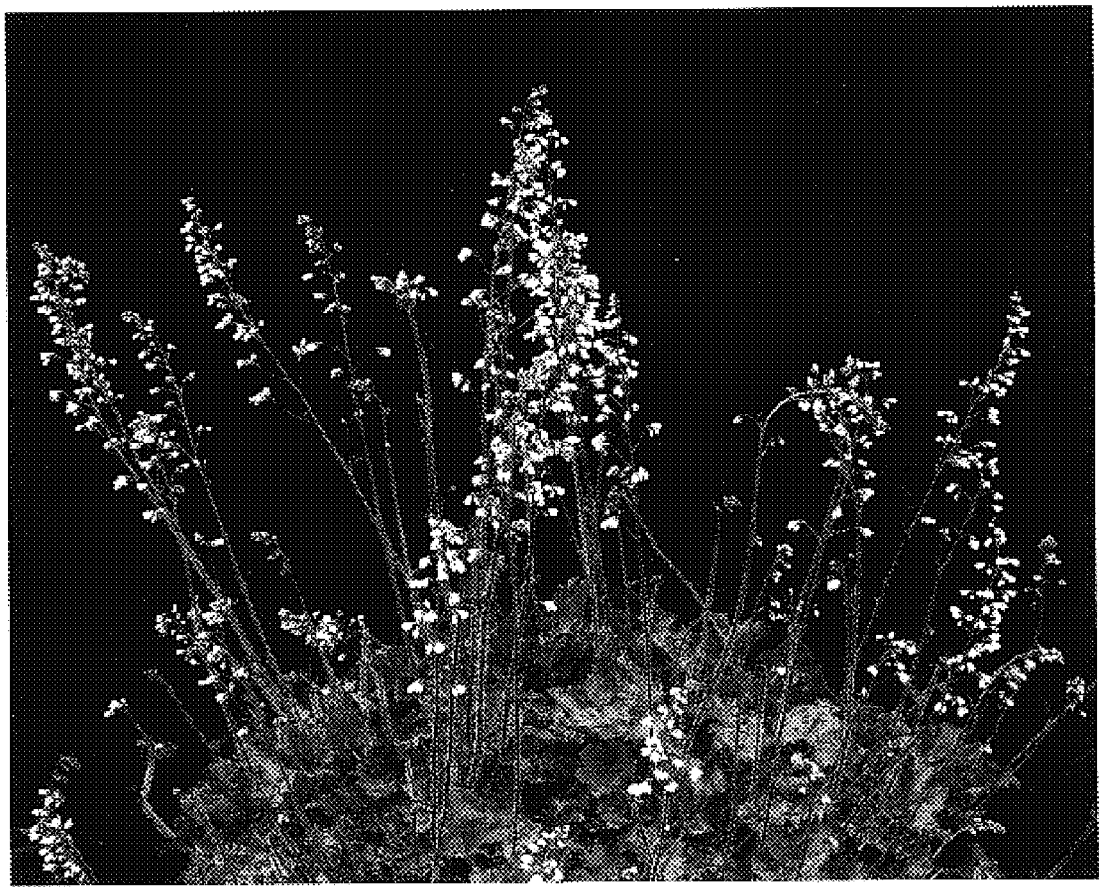

* * * * *